US00PP16628P2

(12) United States Plant Patent
Kobayashi

(10) Patent No.: US PP16,628 P2
(45) Date of Patent: Jun. 13, 2006

(54) POINSETTIA PLANT NAMED 'PER979'

(50) Latin Name: *Euphorbia pulcherrima*
Varietal Denomination: PER979

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 87 days.

(21) Appl. No.: 10/955,486

(22) Filed: Sep. 30, 2004

(51) Int. Cl.
*A01H 5/00* (2006.01)

(52) U.S. Cl. ..... Plt./307
(58) Field of Classification Search ..... Plt./307
See application file for complete search history.

(56) References Cited

U.S. PATENT DOCUMENTS

PP9,854 P * 4/1997 Dummen ..... Plt./307
PP11,109 P * 10/1999 Fruehwirth ..... Plt./307
PP11,229 P * 2/2000 Fruehwirth ..... Plt./307
PP15,883 P2 * 7/2005 Kobayashi ..... Plt./307

OTHER PUBLICATIONS

UPOV ROM GTITM Computer Database, GTI JOUVE Retrieval Software 2005/02 Citation for 'PER979'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of Poinsettia plant named 'PER979', characterized by its inflorescences with large dark red-colored flower bracts; dark green-colored leaves; uniform, compact, upright and mounded plant habit; mid-season flowering; natural season flower maturity date is early December for plants grown in Encinitas, Calif.; and excellent post-production longevity.

1 Drawing Sheet

Botanical designation: *Euphorbia pulcherrima* Willd.
Cultivar designation: 'PER979'.

BACKGROUND OF THE INVENTION

The present Invention relates to a new and distinct cultivar of Poinsettia plant, botanically known as *Euphorbia pulcherrima* Willd., and hereinafter referred to by the name 'PER979'.

The new Poinsettia a product of a planned breeding program conducted by the Inventor in Encinitas, Calif. The objective of the breeding program is to create new mid-season flowering Poinsettia cultivars having strong stems, attractive flower bract coloration, uniform plant habit and excellent post-production longevity.

The new Poinsettia originated from a cross-pollination made by the Inventor in December 1997, of *Euphorbia pulcherrima* Willd. '745', U.S. Plant Pat. No. 11,109, as the female, or seed, parent, with a proprietary selection of *Euphorbia pulcherrima*. Willd. identified as N-33, not patented, as the male, or pollen, parent. The cultivar PER979 was discovered and selected by the Inventor as a single flowering plant within the progeny of the stated cross-pollination in a controlled environment in Encinitas, Calif., in December, 1998.

Asexual reproduction of the new Poinsettia by terminal cuttings propagated in a controlled environment in Encinitas, Calif., since July, 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'PER979'. These characteristics in combination distinguish 'PER979' as a new and distinct cultivar:

1. Inflorescences with large dark red-colored flower bracts.
2. Dark green-colored leaves.
3. Uniform, compact, upright and mounded plant habit.
4. Mid-season flowering; natural season flower maturity date is early December for plants grown in Encinitas, Calif.
5. Excellent post-production longevity.

Plants of the new Poinsettia are similar to plants of the female parent selection, however, plants of the new Poinsettia are not as vigorous as plants of the female parent selection.

Compared to plants of the male parent selection, plants of the new Poinsettia have darker colored leaves and flower bracts, are more vigorous and flower about one week earlier.

Plants of the new Poinsettia can also be compared to plants of the cultivar 490, disclosed in U.S. Plant Pat. No. 7,825. In side-by-side comparisons conducted in Encinitas, Calif., plants of the new Poinsettia differed primarily in time to flower as plants of the new Poinsettia flowered about two weeks later than plants of the cultivar 490.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the top of the sheet comprises a side perspective view of a typical flowering plant of 'PER979' grown in a container.

The photograph at the bottom left of the sheet is a close-up view of a typical inflorescence of 'PER979'.

The photograph at the bottom right of the sheet comprises a top perspective view of a typical plant of 'PER979'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polyethylene-covered greenhouse with day temperatures averaging about 24° C., night temperatures averaging about 19° C. and light levels about 4,000 foot-candles. Single plants were grown in 16.5-cm pots and pinched once. Plants were flowered under natural season short day/long night conditions. Plants were about 17 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar PER979.

Parentage:

*Female parent.*—*Euphorbia pulcherrima* Willd. '745', U.S. Plant Pat. No. 11,109.

*Male parent.*—Proprietary selection of *Euphorbia pulcherrima* Willd. identified as code number N-33, not patented.

Propagation:

*Type cutting.*—Terminal cuttings.

*Time to initiate roots.*—About 10 days at 20° C. to 22° C.

*Time to develop roots.*—About 28 days at 20° C. to 22° C.

*Root description.*—Thick, fibrous, freely-branching; white in color.

Plant description:

*Plant form.*—Inverted triangle; top of plant mounded.

*Growth habit.*—Compact, upright and uniform plant habit. Moderately vigorous.

*Plant height.*—About 25 cm.

*Plant diameter or spread.*—About 37 cm.

*Lateral branch description.*—Quantity: About five lateral branches develop after pinching. Length: About 17 cm. Diameter: About 6 mm. Internode length: About 2.2 cm. Strength: Strong. Texture: Smooth; glabrous. Color: 144A tinged with 187B.

*Foliage description.*—Arrangement: Alternate, single. Length: About 11.5 cm. Width: About 8 cm. Shape: Elliptic. Apex: Acuminate. Base: Attenuate. Margin: Entire with irregular lobing. Venation pattern: Pinnate. Texture, upper and lower surfaces: Glabrous smooth. Surface: Slightly rugose. Aspect: Mostly flat. Orientation: Mostly horizontal to slightly downward. Color: Developing and fully expanded foliage, upper surface: 147A. Developing and fully expanded foliage, lower surface: 147B. Venation, upper and lower surfaces: 147C. Petiole: Length: About 5 cm. Diameter: About 2.5 mm. Texture, upper and lower surfaces: Smooth; glabrous. Color: 187B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Mid-season flowering, response time about 9 weeks; natural season flower maturity date is early December for plants grown in Encinitas, Calif.

*Post-production longevity.*—Plants of the new Poinsettia maintain good substance and bract color for about four weeks under interior conditions.

*Inflorescence size.*—Diameter: About 31 cm. Height (depth): About 5.5 cm.

*Flower bracts.*—Quantity per inflorescence: About 18. Length, largest bracts: About 15 cm. Width, largest bracts: About 10 cm. Shape: Elliptic. Apex: Acuminate. Base: Obtuse. Margin: Entire with irregular lobing. Texture, upper and lower surfaces: Glabrous; velvety. Surface: Initially, rugose, becoming mostly smooth with development. Aspect, Mostly flat. Orientation: Mostly horizontal to slightly upright. Venation pattern: Pinnate. Color: Developing or transitional bracts, upper surface: Darker than 53A. Developing or transitional bracts, lower surface: 53A. Fully developed bracts, upper surface: 45A; color does not fade with development. Fully developed bracts, lower surface: 53B. Venation, upper and lower surfaces: Similar to flower bract color. Bract petiole: Length: About 4.3 cm. Diameter: About 3 mm. Texture, upper and lower surfaces: Smooth; glabrous. Color: 187A.

*Cyathia.*—Quantity per corymb: About ten. Diameter of cyathia cluster: About 3.5 cm. Length: About 1 cm. Width: About 8 mm. Shape: Ovoid. Color, immature: 144A. Color, mature: 144A to 144B. Peduncle: Length: About 2 mm. Diameter: About 2 mm. Strength: Strong. Aspect: Mostly upright. Texture: Smooth, glabrous. Color: 144B. Stamens: Quantity per cyathium: About seven to eight. Anther shape: Bi-lobed. Anther length: About 1 mm. Anther color: 187A. Amount of pollen: Scarce. Pollen color: 11A. Pistils: None observed. Nectaries: Quantity per cyathium: About one or two. Size: About 5 mm by 6 mm. Color: 26A.

Disease/pest resistance: Resistance to pathogens and pests common to Poinsettias has not been observed on plants grown under commercial conditions.

It is claimed:

1. A new and distinct cultivar of Poinsettia plant named 'PER979', as illustrated and described.

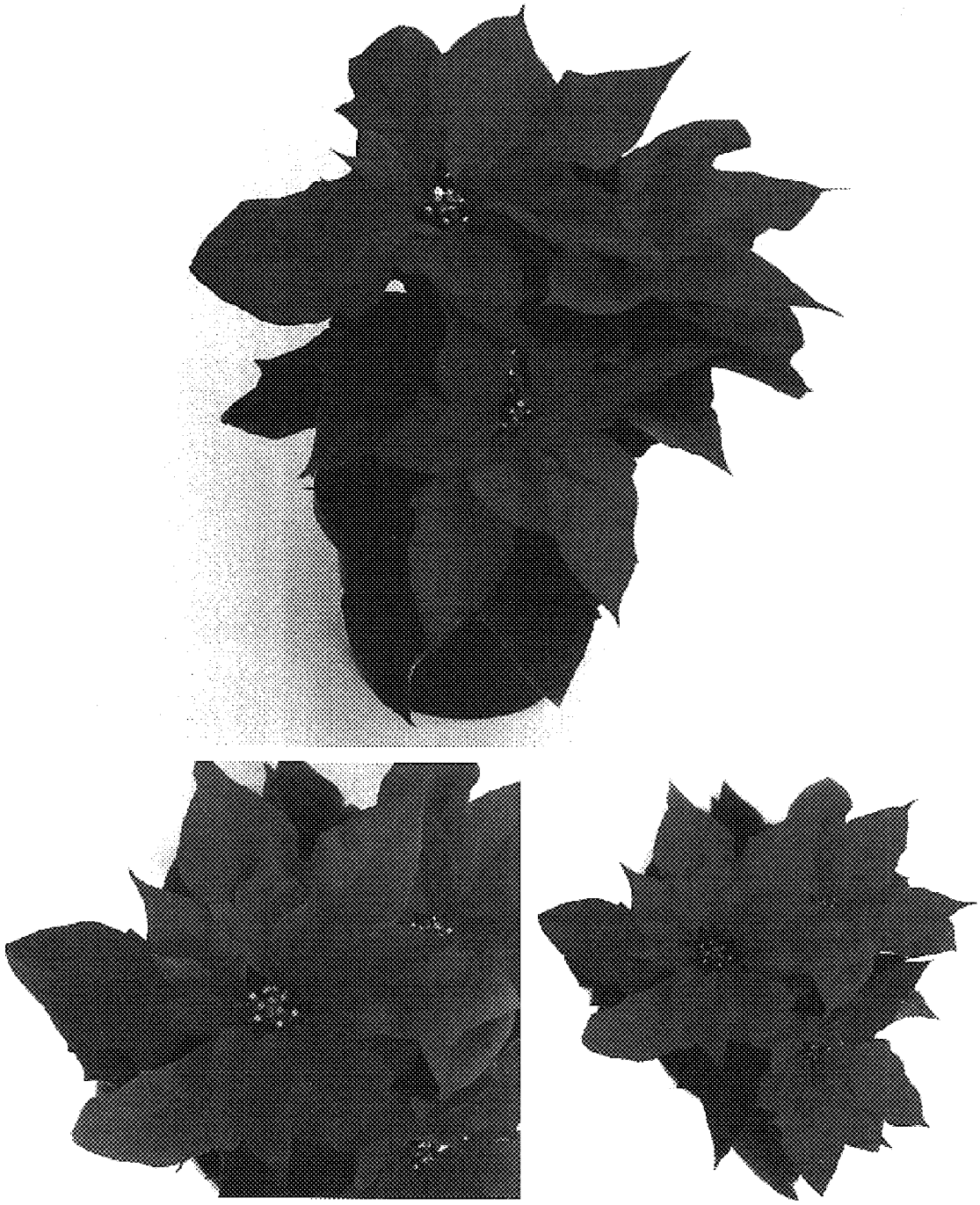

* * * * *